United States Patent [19]

Mazanec et al.

[11] Patent Number: 4,677,091

[45] Date of Patent: Jun. 30, 1987

[54] PROCESS FOR THE PREPARATION OF MIXED METAL OXIDE CATALYSTS

[75] Inventors: Terry J. Mazanec; John G. Frye, Jr., both of Solon, Ohio

[73] Assignee: The Standard Oil Company, Cleveland, Ohio

[21] Appl. No.: 903,912

[22] Filed: Sep. 5, 1986

Related U.S. Application Data

[63] Continuation of Ser. No. 754,881, Jul. 15, 1985, abandoned.

[51] Int. Cl.$^4$ .................. B01J 21/04; B01J 23/04; B01J 23/12
[52] U.S. Cl. .................. 502/182; 502/300; 502/345; 502/346; 518/713
[58] Field of Search .............. 502/182, 300, 324, 340, 502/344, 345, 346; 518/713

[56] References Cited

U.S. PATENT DOCUMENTS

| | | | |
|---|---|---|---|
| 3,519,575 | 7/1970 | Bozik et al. | 502/337 |
| 4,111,847 | 9/1978 | Stiles | 252/463 |
| 4,122,110 | 10/1924 | Sugier et al. | 260/449.5 |
| 4,279,781 | 7/1921 | Dienes et al. | 252/463 |

*Primary Examiner*—W. J. Shine
*Attorney, Agent, or Firm*—Larry W. Evans; David J. Untener; Raymond F. Keller

[57] ABSTRACT

Mixed metal oxide catalysts suitable for the production of alcohols from carbon monoxide and hydrogen are prepared by:

(a) forming a solution of the metals in a polar organic solvent, (b) precipitating the metals from the solution either in the form of their oxides or a form thermally decomposable to the oxides, (c) calcining the precipitate to form the oxides and remove thermally decomposable components therefrom, and (d) where an anion other than oxide remains from step (c) removing same from the precipitate.

Suitable polar organic solvents are ketones, esters, ethers and alcohols, particularly $C_1$ to $C_{10}$ alcohols. Preferably, the precipitated metals are washed with water to remove anions other than oxide. The method is particularly suitable for the production of catalysts containing metals such as uranium which are difficult to precipitate from aqueous solution.

13 Claims, No Drawings

PROCESS FOR THE PREPARATION OF MIXED METAL OXIDE CATALYSTS

This is a continuation of co-pending application Ser. No. 754,881 filed July 15, 1985, now abandoned.

TECHNICAL FIELD

This invention relates to a process for the production of catalysts suitable for the use in the production of alcohols from gas containing carbon monoxide and hydrogen and also to a process for using said catalysts in the production of alcohols.

BACKGROUND OF INVENTION

The use of mixed metal oxide catalysts for the conversion of carbon monoxide and hydrogen to alcohols has been previously described in U.S. Pat. No. 4,298,354 and also in our copending U.S. patent application Ser. No. 653,946. In these patents, the mixed metal oxide catalyst is prepared by coprecipitation of the metal oxides or a form thermally decomposable to the oxides from their aqueous solution by the addition of a precipitating agent such as a hydroxide or carbonate.

The above described process is generally very satisfactory for most metals but it has been found that certain metal compounds, for example, those of uranium, have a high solubility in water, even at pH values above 9, and uranium is for this reason not easily precipitated with the other metals.

Moreover, when an attempt is made to precipitate uranium from aqueous solution together with other metals such as copper it is found that the precipitate contains far less uranium than would be predicted from the amount of uranium compound used to prepare the solution. One consequence of containing only small amounts of uranium is that the selectivity to alcohols containing two or more carbon atoms of the catalyst derived from the precipitate is usually poor.

It is therefore an object of the present invention to provide an improved process for the preparation of a catalyst for the production of alcohols from carbon monoxide and hydrogen.

SUMMARY OF THE INVENTION

According to one aspect of the present invention, a process for the preparation of a mixed metal oxide catalyst suitable for the production of alcohols from carbon monoxide and hydrogen comprises:

(a) forming a solution of the metals in a polar organic solvent, (b) precipitating the metals from the solution either in the form of their oxides or a form thermally decomposable to the oxides, (c) calcining the precipitate to form the oxides and remove thermally decomposable components therefrom, and (d) where an anion other than oxide remains from step (c) removing same from the precipitate.

According to another aspect of the present invention, a process for the preparation of alcohols from carbon monoxide and hydrogen comprises contacting these two gases at superatmospheric pressure and elevated temperature with a mixed metal oxide catalyst precipitated from a polar organic solvent.

DETAILED DESCRIPTION OF THE INVENTION

The polar organic solvent can be a ketone such as acetone, an ester such as methyl acetate, an ether such as tetrahydrofuran or an alcohol such as ethanol.

The precipitation of the metals from the solution in the polar organic solvent is conveniently effected by mixing the solution with a solution of the precipitating agent also in a polar organic solvent.

The term polar organic solvent as used herein is intended to mean a solvent containing at least 50 percent by volume of a polar organic solvent. Water can be present but desirably comprises less than 40 percent by volume of the total and preferably less than 10 percent. Preferably the solvent consists essentially of the polar organic solvent which is preferably an alcohol or mixture of alcohols.

Preferred alcohols are $C_1$ to $C_{10}$ alcohols such as methanol, ethanol, n propanol, i-propanol, n butanol, i butanol, t-butanol, pentanols, hexanols, ethylene glycol, propylene glycol, glycerol or a mixture of these. Methanol is preferred. Small amounts of esters, ethers, alkenes, aromatics, or other solvents can also be present.

The metal compounds dissolved in the polar organic solvent can conveniently be salts such as nitrates, sulfates, halides, phosphates, acetates, other carboxylates or the like. Nitrates are preferred.

The precipitating agent can be a base such as an alkali or alkaline earth metal or ammonium hydroxide, carbonate or bicarbonate or mixture thereof.

The temperature at which the precipitation is effected can vary widely but is conveniently from 10° to about 40° C. The order of addition is not critical.

The calcination is effected to decompose any thermally decomposable compounds especially salts to form the oxide and comprises heating in air to, for example 250° to 750° C., preferably 300° to 450° C. for a sufficient period of time to decompose the compounds and form the oxides. Usually the duration of the calcination is from 1 to 6 hours.

Where an anion or anions other than oxide remains in the calcined solids from step (c) then the calcined solids are treated to remove the anion prior to the use of the catalyst since the presence of anions tends to reduce the activity of the catalyst. The nature of the anion will depend on the metal salts from which the catalyst was precipitated since the source of the anion is the counterion of the metal in the salt used and may be, for example, chloride, nitrate, acetate or phosphate and the like.

The removal of these ions for example chloride, nitrate, acetate and phosphate is conveniently effected by washing with water or other suitable solvent.

Alternatively, the anions may, in suitable cases, be removed by gentle reduction, for example, nitrate and acetate can be removed by gently heating in a stream of a reducing gas such as carbon monoxide or hydrogen. The reduction conditions should be milder, for example, than those employed in Comparative Examples 3 and 4 where an exothermic reaction resulted in the catalyst forming a fused and inactive mass.

The washed catalyst can then be impregnated with an aqueous solution of an alkali or alkaline earth metal ions for example, lithium, sodium, potassium, rubidium, cesium, beryllium, magnesium, calcium, strontium or barium. Suitable compounds for dissolving in water to effect the impregnation are hydroxides, carbonates or bicarbonates. The impregnation is effected so as to leave, when dry, from 0.01 to 20 percent by weight of alkali metal or alkaline earth metal based on the weight of the material, preferably 0.5 to 15.0 percent.

Preferably the catalyst is formed into pellets by incorporation of a binding agent and pressing in a pellet press. Suitable binding agents include graphite, titanium dioxide, thorium dioxide, alumina, or zirconium dioxide. These agents may be used as a colloidal dispersion. Conveniently 1 to 10 percent, preferably 3 to 5 percent of a graphite is useful as a binding agent.

The catalyst can be subjected to a reductive activation treatment before use by contacting with a suitable reducing gas such as hydrogen at a temperature suitable for at least partial reduction of one or more of the metal oxides to a reduced form. Conveniently a dilute stream of hydrogen in nitrogen (15 percent $H_2$, 85 percent $N_2$) is used and the catalyst is charged to a stainless steel tube placed in a programmable furnace capable of slowly raising the temperature from ambient to the highest temperature of the reduction, preferably 250° C. or the temperature at which the catalyst will be used in the subsequent reaction to form alcohols. The reduction is preferably accomplished at about atmospheric pressure although elevated pressures up to about 100 atmospheres can be used.

The feed and process conditions for the production of alcohols are as follows. Although synthesis gas is a preferred reactant, any other gas composed primarily of hydrogen and carbon monoxide and having an $H_2$ to CO ratio of about 1:10 to about 10:1, preferably about 1:3 to about 3:1, can be employed. The gaseous reactant should contain as little sulfur compounds as possible since sulfur is a known poison for copper containing catalysts. Preferably the gaseous reactant is essentially sulfur-free.

The contact time of the reactants with the catalyst is not critical but should be below about 200 seconds and preferably between about 5 and 100 seconds.

The reaction pressure should normally be in the range of about 150 to about 4000 psig, preferably about 750 to about 1000 psig. Although there is no upper limit to the reaction pressure, pressures higher than about 1500 psig or 2000 psig are normally not employed because of the high expense involved. It is preferable to operate at at least about 500 psig because formation of alcohols is favored at higher pressures.

The reaction temperature should be maintained in the range of about 100° to about 500° C., preferably about 220° to about 400° C., and more preferably about 250° to about 325° C.

The invention is illustrated by the following examples.

COMPARATIVE EXAMPLE 1

Preparation of Catalyst A

This Example is comparative in that it omits the step (d) from the catalyst preparation i.e., removal of anions remaining at the end of the calcination step. It will be demonstrated in Comparative Examples 3 and 4 that the product of Comparative Example 1 is inactive as a catalyst.

The proportions of reactants employed were chosen to correspond with a formula of $Cu_{0.75}$-U-$Al_{0.3}$-$K_x$ (a) Precipitation and Filtration In 2.0 liters of methanol were dissolved 50.0 g of copper nitrate ($Cu(NO_3)_2$-$2.5H_2O$), 144.0 g of uranyl nitrate ($UO_2(NO_3)_2$$6H_2O$), and 32.0 g of aluminum nitrate ($Al(NO_3)_3$$9H_2O$). To this solution a second solution of 2.0M potassium hydroxide (KOH) in methanol, was added dropwise, while stirring, over a period of 1 hour. The solution was kept at room temperature (22° C.). When the pH reached 9.50 as measured by a Corning Model 125 pH meter the addition was stopped and enough 2.0M $HNO_3$ was added to the mixture until the pH reached 7.00. The mixture was vacuum filtered on a Buchner funnel and the filter cake was reslurried with 300 ml of methanol and vacuum filtered again. The solids were washed two more times for a total of three washings.

(b) Calcination

The resulting solid was placed in a temperature programmed muffle furnace and heated from room temperature to 400° C. over the course of 10 hours, held at 400° C. for 2 hours, and allowed to cool to room temperature. The material was divided into fractions.

The calcined solid contained
Cu: 6.2 percent
U: 30 percent
Al: 1.0 percent
K: 25 percent corresponding to $CuUAl_{0.29}K_{5.1}O_y$. The surface area was 0.41 m$^2$/g by nitrogen adsorption.

EXAMPLE 1

Preparation of Catalyst B $Cu_{0.75}$-U-$Al_{0.3}$-$K_x$

Washing Catalyst A With Water to Remove Anions, Drying and Pelletizing

One fraction of Catalyst A was washed by placing 70 grams of the solid in a beaker with 250 cc of distilled water. The mixture was stirred vigorously for one hour and the catalyst chunks were completely broken up. The resulting slurry was vacuum filtered using a glass fritted Buchner funnel and washed with three 25 cc portions of distilled water. The filter cake was dried overnight at 120° C. in an oven. A portion of the dried material was submitted for analysis and the remainder was mixed with 3 percent by weight of graphite, pelletized, and sieved to give a 10–30 mesh fraction.

Analysis of the catalyst was:
Cu: 11.0 percent
U: 58 percent
Al: 2.0 percent
K: 7.3 percent corresponding to $Cu_{0.71}UAl_{0.30}K_{0.77}$. The surface area was 55.3 m$^2$/gm.

The purpose of the washing step was to remove anions such as nitrate remaining from the precipitation step. The washing has the effect of additionally removing potassium. The increase in surface area demonstrates that the washing removed material from the pores of the catalyst.

This Example shows a close correspondence for copper, uranium and aluminum between the analyzed formula and the formula calculated from the quantities of reactants.

EXAMPLE 2

Preparation of Catalyst C $Cu_{0.75}$-U-$Al_{0.3}$-$K_x$+3 percent K

Washing Catalyst A to Remove Anions, Impregnating with Potassium and Pelletizing One fraction of Catalyst A was washed by placing it in a beaker with 1 liter of distilled water and stirring for 36 hours. The solid material was separated by vacuum filtration on a medium porosity glass fritted Buchner funnel and washed three times with 100 cc portions of distilled water. The solid was dried overnight at 110° C. to give 36.46 g of material. The dried material was impregnated by adding a solution made from 1.91 g of 85 percent KOH and enough water to make 18 cc of solution. The impregnated material was dried at 110° C. for several hours, pelletized with 3 percent by weight of graphite, and sieved to give a 10–30 mesh fraction.

Analysis of the catalyst was:
Cu: 9.9 percent
U: 53 percent
Al: 2.6 percent
K: 8.2 percent corresponding to $Cu_{0.70}UAl_{0.43}K_{1.0}$. The surface area was 27.1 m²/g determined by nitrogen adsorption.

The purpose of the washing was to remove anions such as nitrate remaining from the precipitation step. The washing had the effect of additionally removing potassium, so that even though 3 percent of potassium was added by impregnation, the potassium content of the impregnated solid was much lower (8.2 percent) than the solid before washing (25 percent). The increase in surface area demonstrates that the washing removes material from the pores of the catalyst.

The product was examined by x-ray diffraction and found to contain potassium uranate.

COMPARATIVE EXAMPLE 2

Catalyst D $Cu_{0.75}$-U-$Al_{0.3}$-$K_x$ (Precipitated in Water)

The proportions of the reactants employed were chosen to correspond to a catalyst of formula $Cu_{0.75}$-U-$Al_{0.3}$-$K_x$.

In 2.0 liters of $H_2O$ were dissolved 50.0 g of copper nitrate ($Cu(NO_3)_2 \cdot 2.5H_2O$), 144.0 g of uranyl nitrate ($UO_2(NO_3)_2 6H_2O$), and 32.0 g of aluminum nitrate ($Al(NO_3)_3 9H_2O$). To this solution a second solution of 2.0M potassium carbonate ($K_2CO_3$) in water, was added dropwise, while stirring, until the pH reached 9.5 as measured by a Corning Model 125 pH meter. The mixture was kept at room temperature (22° C.) throughout. After reaching pH 9.5 the solution was neutralized by addition of a solution of 2.0M $HNO_3$ until the pH reached 7.00. The mixture was vacuum filtered and the filter cake was reslurried with 1 liter of distilled water and filtered again. This was repeated until the filter cake had been washed three times. The solid was placed in a programmable muffle furnace and heated from room temperature to 400° C. over the course of 10 hours, held at 400° C. for two hours, and allowed to cool to room temperature.

Analysis of the solid was:
33 percent Cu
29 percent U
5.8 percent Al
5.3 percent K corresponding to a formula $Cu_{4.26}UAl_{1.76}K_{1.11}$. This illustrates that the proportion of uranium in the catalyst was far lower than would have been expected from the relative amounts of the reactants. This is due to the fact that the uranium is difficult to precipitate from aqueous solution.

EXAMPLE 3

Preparation of Catalyst (a) Precipitation from Methanol and Calcination

The proportions of reactants were chosen to correspond to a formula $Cu_{0.75}UAl_{0.3}K_xO_y$.

50 g of $Cu(NO_3)_2 \cdot 2\frac{1}{2}H_2O$ (0.215 mole of copper), 144 g of $UO_2(NO_3)_2 \cdot 6H_2O$ (0.287 mole of uranium), and 32 g of $Al(NO_3)_3 \cdot 9H_2O$ (0.0853 mole of aluminum) were dissolved in 2 liters of methanol at room temperature. While vigorously stirring the solution, enough 2 molar potassium hydroxide in methanol was added by slow dropwise addition to bring the pH to 7.0. The precipitate was light green in color and was vacuum filtered, then washed once by reslurrying with 2 liters of absolute methanol and refiltering. The filter cake was then dried and calcined in one step by heating as follows: 25° C. to 400° C. at 1° C. per minute and then held at 400° C. for 2 hours and then allowed to cool to room temperature.

(b) Washing to Remove Anions and Impregnation with Potassium

The calcined solid, of mottled brown and yellow appearance was washed by stirring with 1 liter of distilled water for about 12 hours and was then vacuum filtered with a medium glass frit. The solid was washed a further three times while on the frit with 50 ml portions of distilled water and then dried overnight at 110° C. At this stage the material contained 11 percent copper, 56 percent uranium, 2.0 percent aluminum and 5.6 percent potassium. The surface area was 48.9 m²/g. The product was examined by x-ray diffraction and found to contain potassium uranate. This material was then impregnated with a further 3 percent by weight of potassium (as KOH) redried, then pelletized with 3 percent by weight of graphite. The finished catalyst contained 10 percent copper, 54 percent uranium, 1.8 percent aluminum, and 8.7 percent potassium all by weight of the catalyst corresponding to a formula of $Cu_{0.69}UAl_{0.29}K_{1.0}O_y$. The surface area was 17.8 m²/g.

REDUCTION

The reduction/activation of the catalysts was accomplished by charging the desired volume of catalyst to a packed-bed, down-flow reactor consisting of a stainless steel tube encased in an electric furnace and fitted with gas metering apparatus and product collection apparatus. A flow of 0.3 SLPM or $H_2$ and 1.5 SLPM of $N_2$ was set and the reactor heated up by a programmed process controller to go from room temperature to 100° C. in one hour, from 100° to 150° C. in two hours, from 150° to 250° C. in one hour, and held at 250° C. for two hours. The catalyst was permitted to cool to room temperature under the reducing gas before admission of the synthesis gas.

COMPARATIVE EXAMPLE 3

Comparative Examples 3 and 4 illustrate two attempts to use the catalyst A prepared in Comparative Example 1 to prepare methanol and higher alcohols from carbon monoxide and hydrogen.

A 20-cc sample of Catalyst A was charged to the reactor and reduced as described above. The reactor was then pressured up to 1000 psig with an equimolar mixture of CO and $H_2$. The reactor was slowly heated (4° C./min) from room temperature to the desired reaction temperature of 285° C. However, when the reactor temperature reached 220° C., the bed temperature was seen to increase rapidly to as high as 430° C. before the ovens were turned off and the reactor cooled to 170° C. by an external stream of air. This was due to the exothermic oxidation of carbon monoxide to carbon dioxide by residual nitrate in the catalyst. A fused mass was left. The reactor was slowly heated up to 325° C. and maintained at this temperature for one hour. No liquid product was obtained.

COMPARATIVE EXAMPLE 4

A 20-cc sample of Catalyst A was charged to the reactor and reduced as described above. The reactor was then pressured up to 1000 psig with an equimolar mixture of CO and $H_2$. The reactor was slowly heated (4° C./min) from room temperature to the desired reaction temperature of 195° C. under a flow of $H_2$ (0.4 SLPM) and CO (0.4 SLPM). After maintaining the catalyst at 195° C. under a flow of synthesis gas for one hour the cooled collector was opened and no liquid products were obtained.

Comparative Examples 3 and 4 illustrate the deleterious effect of nitrate ions remaining in the catalyst from the calcination step.

EXAMPLES 4 THROUGH 6

A 20-cc sample of Catalyst B prepared in Example 1 was charged to the reactor and reduced as described above. The reactor was pressured up to 1000 PSIG with an equimolar mixture of CO and $H_2$. The reactor was slowly heated (4° C./min) from room temperature to 285° C. under a flow of $H_2$ (0.4 SLPM) and CO (0.4 SLPM) (SV=2400 v/v/h, contact time=54 seconds). After a 90 minute equilibration period, liquids were collected over a one-hour time period. The reactor was heated to 300° C. over 30 minutes, allowed to equilibrate for 30 minutes, and liquids collected for a one-hour run period. The reactor was heated to 325° C. over 30 minutes, allowed to equilibrate for 30 minutes, and liquids collected for a one-hour run period. The results are summarized in Table 1, and together with Comparative Example 3 show the desirability of washing the calcined material free of water soluble salts.

EXAMPLES 7 THROUGH 9

Example 4 was repeated except Catalyst C prepared in Example 2 was used in place of Catalyst B. The results are summarized in Table 1, showing the superiority of catalysts prepared by this technique and doped with alkali.

EXAMPLES 10 THROUGH 12

Example 7 was repeated except that the rates of feed of the gases were adjusted to 1.0 SLPM $H_2$ and 2.0 SLPM CO to give the ratio 0.5 for $H_2$/CO. The results were summarized in Table 1 showing the effect of synthesis gas composition on the catalyst.

EXAMPLES 13 THROUGH 15

Examples 4 through 6 were repeated except that catalyst prepared in Example 3 was used instead of the catalyst of Example 1.

EXAMPLES 16 THROUGH 18

Examples 4 through 6 were repeated except that the hydrogen to carbon monoxide molar ratio was 2:1, the space velocity was 9000 v/v/hour; and the temperature were 200°, 220° and 240° C.

TABLE 1

| | | | | Molar Ratio Hydrogen to Carbon Monoxide 1:1 | | | | | |
| --- | --- | --- | --- | --- | --- | --- | --- | --- | --- |
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro- Carbons | Percent Higher Alcohols |
| 4 | 1 | 7.3 | 0 | 285 | 2400 | 254 | 40 | 4.0 | 15.7 |
| 5 | 1 | 7.3 | 0 | 300 | 2400 | 190 | 52 | 4.2 | 27.2 |
| 6 | 1 | 7.3 | 0 | 325 | 2400 | 138 | 52 | 4.0 | 38.1 |
| 7 | 2 | 8.2 | 3 | 285 | 2400 | 159 | 31 | 7.4 | 19.4 |
| 8 | 2 | 8.2 | 3 | 300 | 2400 | 149 | 40 | 8.1 | 26.7 |
| 9 | 2 | 8.2 | 3 | 325 | 2400 | 130 | 55 | 8.8 | 42.2 |
| 13 | 3 | 8.7 | 3 | 285 | 2400 | 132 | 24 | 6.4 | 18.2 |
| 14 | 3 | 8.7 | 3 | 300 | 2400 | 133 | 32 | 6.1 | 24.3 |
| 15 | 3 | 8.7 | 3 | 325 | 2400 | 121 | 49 | 7.2 | 40.8 |

*Added by impregnation to washed catalyst after calcination.
Pressure 1000 psig

TABLE 2

| | | | | Molar Ratio Hydrogen to Carbon Monoxide 2:1 | | | | | |
| --- | --- | --- | --- | --- | --- | --- | --- | --- | --- |
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro- Carbons | Percent Higher Alcohols |
| | | | | Molar ratio hydrogen: carbon monoxide 2:1 | | | | | |
| 16 | 1 | 7.3 | 0 | 200 | 9000 | 56 | 10 | — | 17.3 |
| 17 | 1 | 7.3 | 0 | 220 | 9000 | 117 | 10 | — | 8.6 |

TABLE 2-continued

| | | Molar Ratio Hydrogen to Carbon Monoxide 2:1 | | | | | | | |
|---|---|---|---|---|---|---|---|---|---|
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro-Carbons | Percent Higher Alcohols |
| 18 | 1 | 7.3 | 0 | 240 | 9000 | 211 | 19 | — | 8.8 |

The above results in Tables 1 and 2 show that potassium can be added by impregnation resulting in an active catalyst.
Pressure 1000 psig

TABLE 3

| | | Molar ratio of hydrogen: carbon monoxide 0.46:1 | | | | | | | |
|---|---|---|---|---|---|---|---|---|---|
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro-Carbons | Percent Higher Alcohols |
| 10 | 2 | 8.2 | 3 | 285 | 9000 | 230 | 51 | 10.1 | 22.1 |
| 11 | 2 | 8.2 | 3 | 300 | 9000 | 264 | 82 | 11.4 | 31.0 |
| 12 | 2 | 8.2 | 3 | 325 | 9000 | 269 | 146 | 16.3 | 54.3 |

The above results show that using a feed with a higher proportion of carbon monoxide yields a product having a higher proportion of higher alcohols and a higher ratio of higher alcohols to hydrocarbons.
*Added by impregnation to washed catalyst after calcination.
Pressure 1000 psig

EXAMPLE 19

Preparation of Catalyst E containing Cu-Zr-Mn and sodium

In 2.0 liters of methanol were dissolved 75.0 g of copper nitrate ($Cu(NO_3)_2 \cdot 2.5H_2O$), 87.0 g of zirconyl nitrate ($ZrO(NO_3)_2 \cdot xH_2O$, 50 percent $ZrO_2$), and 48.0 g of a 50 percent solution of manganous nitrate (50 percent by weight $Mn(NO_3)_2$) in water. To the vigorously stirred solution was added a solution of 2.0M sodium hydroxide (NaOH) in methanol until the pH read 7.00 as measured by a Corning Model 125 pH meter. The mixture was vacuum filtered and the filter cake was calcined by slowly heating from room temperature to 400° C. in a programmable muffle furnace, and maintaining the temperature at 400° C. for two hours. After cooling, the solid was reslurried with 500 cc of water and vacuum filtered. The solid was dried overnight at 120° C. The solid had an analysis of Cu: 29 percent
Zr: 28 percent
Mn: 11 percent
Na: 0.77 percent The solid was impregnated with 2 percent Na by adding a measured amount of a dilute aqueous NaOH solution. This Na-doped fraction was pelleted with 3 percent graphite, crushed and sieved to give a 10–30 mesh fraction.

EXAMPLES 20 THROUGH 22

Examples 4 through 6 were repeated except that Catalyst E doped with sodium prepared by Example 19 was used in place of Catalyst B and the products were collected for two hour time intervals rather than one hour. The results are summarized in Table 4.

These results demonstrate that the preparative technique of the invention can be applied to copper/zirconium catalysts and that the resulting catalyst is active for the production of higher alcohols i.e., alcohols containing two or more carbon atoms as well as methanol.

TABLE 4

| Alcohol Synthesis Results Over Cu—Zr—Mn—Alkali Catalysts | | | | | |
|---|---|---|---|---|---|
| Example or Experiment | Catalyst | Temp. °C. | Productivity g/l/hr | Percent Higher Alcohols | Higher Alcohol/ Hydrocarbon |
| Example 20 | E* (from Example 19) | 285 | 255 | 21.0 | 3.61 |
| 21 | | 300 | 202 | 29.8 | 3.61 |
| 22 | | 325 | 132 | 41.8 | 3.56 |

*according to invention

EXAMPLE 23

Preparation of Catalyst

The proportions of the reactants employed were chosen to correspond to a catalyst of the formula

$$Cu_{1.5}UAl_{0.2}K_xO_y$$

100 g of $Cu(NO_3)_2 \cdot 2\frac{1}{2}H_2O$, 144 g of $UO_2(NO_3)_2 \cdot 6H_2O$ and 22.0 g of $Al(NO_3)_3 \cdot 9H_2O$ were dissolved in two liters of methanol. A two molar KOH in methanol solution was then added to the mixture over a period of one hour and 15 minutes until the pH was 7.0. The mixture was then vacuum filtered and the filter cake placed in a room temperature oven and slowly heated to 400° C. and calcined at that temperature for two hours. After cooling to room temperature the catalyst was then ground to a powder and dispersed in one liter of distilled water. The catalyst mixture was then vacuum filtered and the filter cake reslurried with one liter of distilled water and again vacuum filtered. The catalyst was then placed in an oven at 120° C. and dried overnight. The catalyst was split into four portions. One portion was designated 23A. Catalyst 23A had the following analysis:

Cu: 19 percent
U: 51 percent
Al: 1.2 percent
K: 8.4 percent corresponding to a formula of $Cu_{1.4}UAl_{0.2}K_{1.0}$. Another portion was doped by adding a solution of KOH in distilled water until an additional 3 percent potassium $K^+$ was added. The doped catalyst was then dried in an oven at 120° C. The catalyst was pelletized with 3 percent graphite and designated 23B. Catalyst 23B had the following analysis:

Cu: 17 percent
U: 47 percent
Al: 1.1 percent
K: 10.0 percent corresponding to a formula of $Cu_{1.4}UAl_{0.2}K_{1.3}$. A second portion of catalyst was doped by adding a solution of Na OH in distilled water until the added sodium level reached 1.5 percent. The doped catalyst was then dried in an oven at 120° C. and pelletized with 3 percent graphite and designated 23C. Catalyst 23C had the following analysis:

Cu: 17 percent
U: 46 percent
Al: 1.1 percent
K: 7.6 percent
Na: 1.4 percent corresponding to a formula $Cu_{1.4}UAl_{0.2}K_{1.0}Na_{0.3}$. Another portion of the catalyst was doped by adding a solution of Cs OH in distilled water until the cesium level reached 9 percent. The doped catalyst was then dried in an oven at 120° C., pelletized with 3 percent graphite and designated 23D. Catalyst 23D had the following analysis:

Cu: 16 percent
U: 42 percent
Al: 0.97 percent
K: 6.7 percent
Cs: 8.3 percent corresponding to a formula of $Cu_{1.4}UAl_{0.2}K_{1.0}Cs_{0.4}$.

EXAMPLE 24

Preparation of Catalyst

The proportions of the reactants employed were chosen to correspond to a catalyst of the formula $Cu_{1.5}UAl_{0.2}K_xO_y$.

The catalyst preparation of Example 23 was repeated exactly as far as the drying at 120° C. except the calcination was effected at 350° C. and the water washing was effected by reslurrying in two liters of distilled water once only.

One portion of this catalyst (26.70 g) was impregnated with a solution of KOH in distilled water until the added $K^+$ level reached 3 percent. The catalyst was then dried at 120° C. in an oven for two hours and pelletized with 3 percent graphite and designated Catalyst 24.

EXAMPLE 25

Catalyst Preparation

The proportions of the reactants employed were chosen to correspond to a formula of $Cu_{1.5}UAl_{0.2}Ba_xO_yK_z$ 50.0 g of $Cu(NO_3)_2\cdot2\frac{1}{2}H_2O$, 72.26 g of $UO_2(NO_3)_2\cdot6H_2O$ and 10.80 g of $Al(NO_3)_3\cdot9H_2O$ were dissolved in one liter of methanol. 14.21 g of $BaCO_3$ was then added to the solution. A 2M solution of KOH in methanol was then added over a period of about one hour and 30 minutes until the pH was 9.90. The mixture was then vacuum filtered, the filtercake reslurried with one liter of methanol and vacuum filtered again. The solid was then placed in a room temperature furnace and slowly heated to 350° C. and calcined at that temperature for two hours and cooled to room temperature. The solid was ground to a powder and dispersed in one liter of distilled water. The solid was then vacuum filtered and the filtercake dried in an oven at 120° C. The finished material was designated Catalyst 25.

Analysis of Catalyst 25 was:
Cu: 18 percent
U: 48 percent
Al: 1.0 percent
K: 4.5 percent
Ba: 6.7 percent corresponding to a formula of: $Cu_{1.4}UAl_{0.18}K_{0.57}Ba_{0.24}$. This Example shows that the atomic proportions of Cu and U are close to the formula calculated from the weights of salts dissolved.

X-ray diffraction data for the catalysts prepared as described above is summarized in Table A.

The catalysts prepared in Examples 23, 24 and 25 were tested for activity and the results are summarized in Tables 5-7.

TABLE A

X-Ray Diffraction Data for Cu—Catalysts

| Compound | | 23A | 23B | 23C | 23D | 25 |
|---|---|---|---|---|---|---|
| 7.01 A | K2 U4 O13 | na | na | 0 | 0 | 66 |
| 6.60 A | K2 U2 O7 | na | na | 135 | 130 | 16 |
| 3.78 A | K NO3 | 0 | 0 | 0 | 0 | 0 |
| 3.48 A | K2U4O13/CuUO4 | 45 | 45 | 45 | 43 | 100 |
| 3.37 A | Graphite | 10 | 110 | 105 | 80 | 0 |
| 3.28 A | K2U2O7/CuU3O10 | 100 | 100 | 100 | 100 | 15 |
| 3.12 A | K2U4O13 | 10 | 5 | 15 | 5 | 85 |
| 2.85 A | K2U2O7/CuUO4 | 15 | 15 | 20 | 20 | 0 |
| 2.62 A | K2U2O7 | 3 | 3 | 2 | 5 | 5 |
| 2.53 A | CuO | 12 | 12 | 12 | 15 | 10 |
| 2.33 A | CuO | 15 | 13 | 15 | 15 | 18 |
| 2.19 A | K2U2O7 | 10 | 12 | 12 | 14 | 0 |
| 2.02 A | K2U2O7 | 20 | 25 | 25 | 30 | 21 |
| 1.92 A | K2U2O7/CuUO4/CuU3O10 | 12 | 8 | 12 | 15 | 25 |
| 1.87 A | CuO | 2 | 2 | 2 | 2 | 15 |

The figures in the Table show the relative intensities of the x-ray lines. The strong lines at 6.60 A and 7.01 A show the presence of significant amounts of (i) $K_2U_2O_7$ in Catalysts 23C and 23D and (ii) the presence of $K_2U_4O_{13}$ in Catalyst 25 respectively.

Since all the Catalysts 23A, 23B, 23C and 23D were prepared by the same technique (apart from the impregnation) it is concluded that they all contain potassium uranates.

TABLE 5

Alcohol Synthesis Results Over Cu1.5-U—Al0.2-Ax—Oy Catalysts

| Example No. | 26 | 27 | 28 | 29 | 30 | 31 |
|---|---|---|---|---|---|---|
| Cat. No. | 23C | 23C | 23C | 23D | 23D | 23D |
| Temp °C. | 285.0 | 300.0 | 325.0 | 285.0 | 300.0 | 325.0 |
| Press psig | 1000.0 | 1000.0 | 1000.0 | 1000.0 | 1000.0 | 1000.0 |
| SV h-1 | 4800.0 | 4800.0 | 4800.0 | 4800.0 | 4800.0 | 4800.0 |
| CT sec | 26.9 | 26.2 | 25.1 | 26.9 | 26.2 | 25.1 |
| Time Hours | 2.0 | 2.0 | 2.0 | 2.0 | 2.0 | 2.0 |
| Liq Wt Grams | 5.3 | 5.0 | 4.1 | 4.3 | 3.1 | 1.5 |
| Percent C1OH | 72.3 | 59.2 | 39.5 | 81.3 | 72.7 | 54.8 |
| C2OH | 7.7 | 8.5 | 7.2 | 7.5 | 9.0 | 6.1 |
| n-C3OH | 4.3 | 8.3 | 16.1 | 7.4 | 10.7 | 9.3 |
| i-C3OH | 0.4 | 0.4 | 0.5 | 0.5 | 0.0 | 0.0 |
| n-C4OH | 2.5 | 3.4 | 3.4 | 1.9 | 2.8 | 1.7 |
| i-C4OH | 0.5 | 0.9 | 3.9 | 1.0 | 2.7 | 3.5 |
| n-C5OH | 0.4 | 0.5 | 0.6 | 0.4 | 0.7 | 0.0 |
| i-C5OH | 0.8 | 1.6 | 0.0 | 0.0 | 0.0 | 2.2 |
| n-C6OH | 0.2 | 0.3 | 0.4 | 0.0 | 0.6 | 0.8 |

TABLE 5-continued

Alcohol Synthesis Results Over Cu1.5-U—Al0.2-Ax—Oy Catalysts

| Example No. | 26 | 27 | 28 | 29 | 30 | 31 |
|---|---|---|---|---|---|---|
| i-C6OH | 0.0 | 0.5 | 0.8 | 0.0 | 0.7 | 1.1 |
| Wt CH4 Grams | 0.1 | 0.2 | 0.2 | 0.1 | 0.1 | 0.1 |
| Wt CO2 Grams | 2.6 | 3.5 | 4.9 | 2.4 | 2.0 | 2.0 |
| C-BAL | 98.0 | 94.6 | 92.0 | 92.5 | 90.0 | 84.0 |
| Prod-g/l/hr | 264.0 | 249.0 | 204.0 | 213.0 | 155.0 | 74.0 |
| Prod-Hi Alc | 44.0 | 61.0 | 67.0 | 40.0 | 42.0 | 18.0 |
| HA/HC | 6.9 | 6.6 | 5.7 | 7.8 | 10.3 | 4.8 |

The molar ratio of hydrogen to carbon monoxide fed was 1:1 in all cases.

TABLE 6

Alcohol Synthesis Results Over Cu1.5-U—Al0.2-Ax—Oy Catalysts

| Example No. | 32 | 33 | 34 | 35 | 36 | 37 | 38 | 39 |
|---|---|---|---|---|---|---|---|---|
| Cat. No. | 23B | 23B | 23B | 24 | 24 | 24 | 24 | 24 |
| Temp °C. | 285.0 | 300.0 | 325.0 | 275.0 | 275.0 | 275.0 | 275.0 | 275.0 |
| Press psig | 1000.0 | 1000.0 | 1000.0 | 1500.0 | 1500.0 | 1500.0 | 1500.0 | 1500.0 |
| SV h-1 | 4800.0 | 4800.0 | 4800.0 | 9000.0 | 9000.0 | 9000.0 | 9000.0 | 9000.0 |
| CT sec | 26.9 | 26.2 | 25.1 | 21.9 | 21.9 | 21.9 | 21.9 | 21.9 |
| Time Hours | 2.0 | 2.0 | 2.0 | 2.0 | 4.0 | 4.0 | 8.0 | 8.0 |
| Liq Wt Grams | 5.2 | 4.6 | 4.3 | 13.1 | 23.9 | 23.5 | 35.5 | 30.0 |
| Percent C1OH | 72.4 | 72.1 | 42.4 | 81.8 | 73.2 | 81.9 | 76.2 | 68.0 |
| C2OH | 8.1 | 10.3 | 7.2 | 5.0 | 4.1 | 4.3 | 3.9 | 3.4 |
| n-C3OH | 4.2 | 11.2 | 17.5 | 2.9 | 2.2 | 2.4 | 2.1 | 1.8 |
| i-C3OH | 0.4 | 0.0 | 0.5 | 0.0 | 0.2 | 0.0 | 0.0 | 0.2 |
| n-C4OH | 2.3 | 3.5 | 2.9 | 1.5 | 1.1 | 1.2 | 1.0 | 0.8 |
| i-C4OH | 0.4 | 1.3 | 5.2 | 0.0 | 0.1 | 0.0 | 0.0 | 0.1 |
| n-C5OH | 0.4 | 0.6 | 0.8 | 0.0 | 0.0 | 0.0 | 0.0 | 0.1 |
| i-C5OH | 0.8 | 0.0 | 3.2 | 0.0 | 0.0 | 0.0 | 0.7 | 0.6 |
| n-C6OH | 0.4 | 0.4 | 0.6 | 0.7 | 0.0 | 0.0 | 0.0 | 0.2 |
| i-C6OH | 0.0 | 0.6 | 0.9 | 0.4 | 0.0 | 0.0 | 0.0 | 0.0 |
| Wt CH4 Grams | 0.1 | 0.2 | 0.2 | 0.2 | 0.4 | 0.3 | 0.5 | 0.5 |
| Wt CO2 Grams | 2.4 | 3.6 | 5.0 | 3.0 | 4.7 | 4.5 | 6.0 | 7.1 |
| C—Bal | 93.3 | 95.1 | 94.5 | 91.7 | 89.0 | 90.5 | 76.7 | 91.8 |
| Prod-g/l/hr | 257.0 | 229.0 | 213.0 | 655.0 | 597.0 | 587.0 | 444.0 | 375.0 |
| Prod-Hi Alc | 43.0 | 64.0 | 83.0 | 69.0 | 46.0 | 46.0 | 33.0 | 27.0 |
| HA/HC | 6.7 | 7.1 | 7.7 | 6.5 | 5.2 | 5.4 | 5.9 | 4.3 |
| Hours on Stream | | | | 4.0 | 12.0 | 20.0 | 36.0 | 56.0 |

For Examples 32-34 the molar ratio of hydrogen to carbon monoxide fed was 1:1, for Examples 35-44 the ratio was 2:1.

TABLE 7

Alcohol Synthesis Results Over Cu1.5-U—Al0.2-Ax—Oy Catalysts

| Example No. | 40 | 41 | 42 | 43 | 44 |
|---|---|---|---|---|---|
| Cat. No. | 24 | 24 | 25 | 25 | 25 |
| Temp °C. | 275.0 | 275.0 | 240.0 | 260.0 | 260.0 |
| Press psig | 1500.0 | 1500.0 | 1000.0 | 1000.0 | 1000.0 |
| SV h-1 | 9000.0 | 9000.0 | 9000.0 | 9000.0 | 36000.0 |
| CT sec | 21.9 | 21.9 | 15.6 | 15.0 | 3.8 |
| Time Hours | 8.0 | 8.0 | 1.0 | 1.0 | 1.0 |
| Liq Wt Grams | 34.0 | 35.3 | 2.5 | 7.7 | 2.8 |
| Percent C1OH | 68.0 | 76.9 | 91.3 | 91.5 | 90.6 |
| C2OH | 3.3 | 3.5 | 4.9 | 4.8 | 3.5 |
| n-C3OH | 1.7 | 1.9 | 0.7 | 1.1 | 0.7 |
| i-C3OH | 0.2 | 0.0 | 0.3 | 0.4 | 0.3 |
| n-C4OH | 0.7 | 0.7 | 0.1 | 0.4 | 0.2 |
| i-C4OH | 0.1 | 0.0 | 0.0 | 0.1 | 0.1 |
| n-C5OH | 0.0 | 0.0 | 0.0 | 0.1 | 0.0 |
| i-C5OH | 0.5 | 0.5 | 0.0 | 0.1 | 0.0 |
| n-C6OH | 0.2 | 0.0 | 0.0 | 0.0 | 0.0 |
| i-C6OH | 0.0 | 0.0 | 0.0 | 0.0 | 0.0 |
| Wt CH4 Grams | 0.5 | 0.4 | 0.1 | 0.1 | 0.1 |
| Wt CO2 Grams | 6.2 | 5.6 | 0.3 | 0.9 | 0.3 |
| C-Bal | 91.6 | 89.2 | 102.7 | 112.7 | 109.8 |
| Prod-g/l/hr | 424.0 | 442.0 | 252.0 | 771.0 | 1136.0 |
| Prod-Hi Alc | 28.0 | 29.0 | 16.0 | 57.0 | 58.0 |
| HA/HC | 5.3 | 5.9 | 2.9 | 6.2 | 2.5 |
| Hours on Stream | 76.0 | 96.0 | | | |

In the above Tables, the following abbreviations and terms mean:

SV: means space velocity, in volumes of gas fed (carbon monoxide and hydrogen) per volume of catalyst per hour.

CT: means contact time in seconds of the reactant gas calculated at reaction conditions.

Time: is the duration of the product collection in hours.

Liq Wt: means the weight in grams of the liquid product collected.

Percent C1OH: means the weight percent of C1OH (methanol) in the liquid product.

C2OH: means ethanol.

i-C3OH: means isopropanol.

n-C3OH: means 1-propanol.

n-C4OH: means 1-butanol.

i-C4OH: means 2-methyl propanol.

n-C5OH: means 1-pentanol.

i-C5OH: means 2-methyl-1-butanol.

n-C6OH: means 1-hexanol.

i-C6OH: means 2-methyl-1-pentanol.

C-BAL: is 100×(moles of carbon recovered/moles of carbon fed)

Prod-g/l/hr: means productivity measured as grams of liquid per liter of catalyst per hour.

Prod-Hi Alc: means productivity of $C_2$ and higher alcohols measured in terms per liter of catalyst per hour.

HA/HC: means the weight of $C_2$ and higher alcohols divided by the weight of hydrocarbons.

The above results show that the catalysts containing copper and uranium prepared by the technique according to the invention are active for the preparation of alcohols from syn gas.

We claim:

1. A process for the preparation of uranium-containing mixed metal oxide catalyst suitable for the production of alcohols from carbon monoxide and hydrogen which process comprises:
   (a) forming a solution of a compound of the metals in a polar organic solvent, (b) precipitating the metals from the solution either in the form of their oxides or a form thermally decomposable to the oxides, (c) calcining the precipitate to form the oxides and remove thermally decomposable components therefrom, and (d) removing anions other than oxides remaining in the precipitate.

2. The process as claimed in claim 1 wherein the polar organic solvent is selected from the group consisting of ketones, esters, ethers and alcohols.

3. The process as claimed in claim 1 wherein the polar organic solvent is a $C_1$ to $C_{10}$ alcohol.

4. The process as claimed in claim 1 wherein the anion is removed by washing the calcined precipitate from step (c) to remove water soluble components therefrom.

5. The process as claimed in claim 1 which comprises impregnating the precipitate with a solution of an alkali metal compound or alkaline earth metal compound.

6. The process as claimed in claim 1 which comprises subjecting the calcined precipitate to a reduction treatment by heating in a stream of a reducing gas.

7. The process as claimed in claim 1 wherein the precipitating of the metals from the solution either in the form of their oxides or a form thermally decomposable to the oxides is effected by mixing the solution of compounds of the metals in the polar organic solvent with a solution of precipitating agent also in a polar organic solvent.

8. The process as claimed in claim 1 wherein the precipitating agent is selected from the group consisting of hydroxides, carbonates and bicarbonates.

9. The process as claimed in claim 1 which comprises forming the calcined precipitate into pellets with a binder.

10. The process as claimed in claim 9 wherein the binder is graphite and is employed in an amount of 1 to 10 percent by weight based on the weight of the catalyst.

11. The process as claimed in claim 1 which comprises forming a solution of salts of the metals in the polar organic solvent the salts being selected from the group consisting of nitrates, sulfates, halides, phosphates and acetates.

12. The process as claimed in claim 1 wherein the mixed metal oxide catalyst contains the oxides of copper and uranium.

13. The process of claim 12 wherein the mixed metal oxide catalyst also contains oxides of Al and one or more alkali metals.

* * * * *